US006001092A

United States Patent [19]
Mirigian et al.

[11] Patent Number: 6,001,092
[45] Date of Patent: *Dec. 14, 1999

[54] COMPLEX COILS HAVING FIBERED CENTERS

[75] Inventors: Gregory E. Mirigian, Fremont; Nga Thi Van, Santa Clara; Son M. Gia, San Jose, all of Calif.

[73] Assignee: Target Therapeutics, Inc., Fremont, Calif.

[ * ] Notice: This patent is subject to a terminal disclaimer.

[21] Appl. No.: 08/909,679

[22] Filed: Aug. 12, 1997

Related U.S. Application Data

[63] Continuation of application No. 08/540,354, Sep. 29, 1995, Pat. No. 5,700,258, which is a continuation-in-part of application No. 08/265,188, Jun. 24, 1994, Pat. No. 5,549,624.

[51] Int. Cl.[6] .................................................. A61B 17/00
[52] U.S. Cl. .................................................................. 606/1
[58] Field of Search ............................... 606/1, 108, 157, 606/191–200; 623/1, 11, 12

[56] References Cited

U.S. PATENT DOCUMENTS 4,994,069  2/1991  Ritchart et al. .
5,700,258  12/1997  Mirigian et al. ............................ 606/1

FOREIGN PATENT DOCUMENTS

WO 94/10936  5/1994  WIPO .

*Primary Examiner*—Glenn K. Dawson
*Attorney, Agent, or Firm*—Morrison & Foerster, LLP

[57] ABSTRACT

A vasoocclusive device in the form of a coil for placement in the vasculature of an animal to form thrombus in a selected site such as an aneurysm or AVM. The device involves a primary coil form having thrombogenic fibers placed on the coil in a specified fashion. The coil will pass through the lumen of a vascular catheter in the primary coil form and evolve into a convoluted or complex secondary form when ejected from the catheter's distal end. The fibers are attached to the coil and cooperate with the coil so that upon ejection from the catheter, the convoluted coil forms a shape in which the central region or secondary coil form center that contains the majority of these fibers.

10 Claims, 5 Drawing Sheets

COMPLEX COILS HAVING FIBERED CENTERS

RELATED APPLICATIONS

This is a continuation of U.S. Ser. No. 08/540,354 filed Sep. 29, 1995, now U.S. Pat. No. 5,700,258 to Mirigian et al., filed Sep. 29, 1995, which is a continuation-in-part of U.S. Ser. No. 08/265,188, now U.S. Pat. No. 5,549,624, issued Aug. 27, 1996, to Mirigian and Van, filed Jun. 24, 1994, the entirety of which is incorporated by reference.

FIELD OF THE INVENTION

This invention is a vasoocclusive device. It is a helically wound coil placed in the vasculature of an animal to form thrombus in a selected site such as an aneurysm or AVM. The device involves a primary coil form having thrombogenic fibers placed on the coil in a specified fashion. The coil will pass through the lumen of a vascular catheter in the primary coil form and evolve into a convoluted or complex secondary form when ejected from the catheter's distal end. The fibers are attached to the coil and cooperate with the coil so that upon ejection from the catheter, the convoluted coil forms a shape in which the central region or secondary coil form center that contains the majority of these fibers.

BACKGROUND OF THE INVENTION

Vasoocclusive devices are surgical implants placed within blood vessels or vascular cavities, typically by the use of a catheter, to form a thrombus and occlude the site. For instance, treatment of a stroke or other such vascular accident may include the placement of a vasoocclusive device proximal of the site to block the flow of blood to the site and alleviate the leakage. An aneurysm may similarly be treated by introduction of a vasoocclusive device through the neck of the aneurysm. The thrombogenic properties of the vasoocclusive device causes a mass to form in the aneurysm and alleviates the potential for growth of the aneurysm and its subsequent rupture. Other diseases, such as tumors, may often be treated by occluding the blood flow to the tumor.

There are a variety of vasoocclusive devices suitable for forming thrombus. One such device is found in U.S. Pat. No. 4,994,069, to Ritchart et al., the entirety of which is incorporated by reference. That patent describes a vasoocclusive coil that assumes a linear helical configuration when stretched and a folded convoluted configuration when relaxed. The stretched configuration is used in placement of the coil at the desired site and the convoluted configuration occurs when the coil is ejected from the catheter and the coil relaxes.

There have been increasing needs to increase the inherent thrombogenicity of these devices. One way of increasing that thrombogenicity is to increase the amount of fiber found in the device. U.S. Pat. No. 5,226,911, to Chee et al., describes a vasoocclusive coil with attached fibrous elements. The fibers are looped in a generally serpentine manner along the coil. The fibrous loops are affixed to (or looped through) the coil at spaced intervals along the coil. The use of multiple fibrous windings is noted in the patent but that use is said to involve placement of the fibers 180° apart on the circumference of the coil.

It should be noted that additional filaments on the exterior of the coil increase the friction of the fibrous coil against the catheter lumen. Added filaments increase the desired thrombogenicity. It is this balance which is difficult to make. We have found a way to increase the overall thrombogenicity without substantially affecting the friction of the inventive coil against the deployment catheter.

DESCRIPTION OF THE INVENTION

As has been noted above, this invention is a vasoocclusive device and, in particular, it is a fibered coil having a complex shape and a majority of the fibers located on the interior of the complex shape. There are three variations of the general concept of this device described below. The first variation is a coil in which the attached fibers are comparatively lengthy and are looped along the primary form of the coil so that when the coil assumes its secondary or complex form, the fibers reside mainly in the center region of the complex. A second variation involves a coil in which the attached fibers are tufts and are situated so that the resulting complex coil includes a center region of the complex coil. The third variation is a coil in which a portion of the axial length of the primary coil includes fibers. The complex form of the coil is designed so that the portion of the coil having fibers evolves into a position which is located centrally within the complex coil center.

Figure 1:
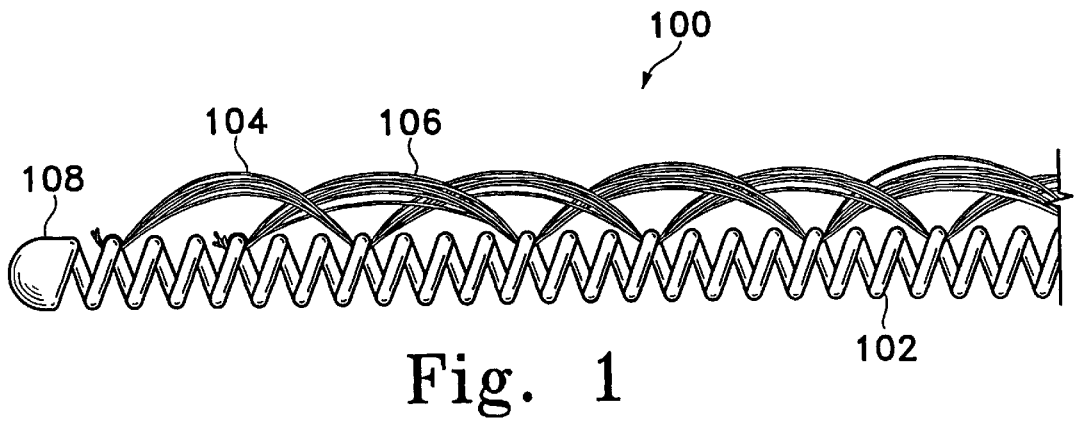
FIG. 1 shows a partial side view of a typical coil (expanded) made according to the invention.

The first variation noted above is discussed with regard to FIGS. 1–6. FIG. 1 shows a length of the fibered coil (100). It is made of several components: a helical coil (102), a first fibrous element (104), and a second fibrous element (106). The end of the coil may be sealed to form a cap (108).

The helical coil (102) is typically of a radiopaque material such as tungsten, tantalum, gold platinum, and alloys of those materials. Stainless steels are also suitable. The use of various polymers, such as polyethylene, polyurethane, and the like as the coil material is also contemplated. The use of polymeric materials typically involves the use of known radiopaque fillers such as powdered tantalum, powdered tungsten, barium sulfate, bismuth oxide, bismuth carbonate, or the like. Preferred, however, is an alloy of platinum with a minor amount of tungsten. This alloy is very flexible and yet the tungsten takes away a measure of ductility from the resulting coil.

The coil may be from 0.2 to 100 cm in length or more. The diameter of the coil is from 0.004" to 0.015", typically from 0.008" to 0.012". The wire making up the coil is 0.0005" to 0.002" in diameter. The coil may be wound to have a tight pitch, that is to say, that there is no space between the adjacent turns of the coil, or it may have some space between adjacent turns. Most desirable, from the point of view of having a high content of fiber, is a coil which is slightly stretched in the manner and in the amount described below.

The first (104) and second (106) fibrous elements typically are bundles of individual fibers (5 to 100 fibers per bundle), but may be individual fibers. The fibers may be of a number of different thrombogenic materials. Suitable synthetic fibers include polyethylene terephthalate (e.g., DACRON), polyesters, especially polyamides (e.g., the Nylons), polyglycolic acid, polylactic acid, and the like. Other less desirable synthetic polymers, because of their decreased thrombogenicity, include fluorocarbons (Teflon) and polyaramids (Kevlar). Natural fibers such as silk and cotton are also quite suitable.

The fibered coil (100) shown in FIG. 1 is in the general shape as found in the catheter lumen. The coil (102) has been stretched to place the first fibrous element (104) and second fibrous element (106) close along the outer periphery of the coil (102). This stretching lessens the overall diameter of the fiber coil (100) as seen by the catheter lumen.

Figure 2:
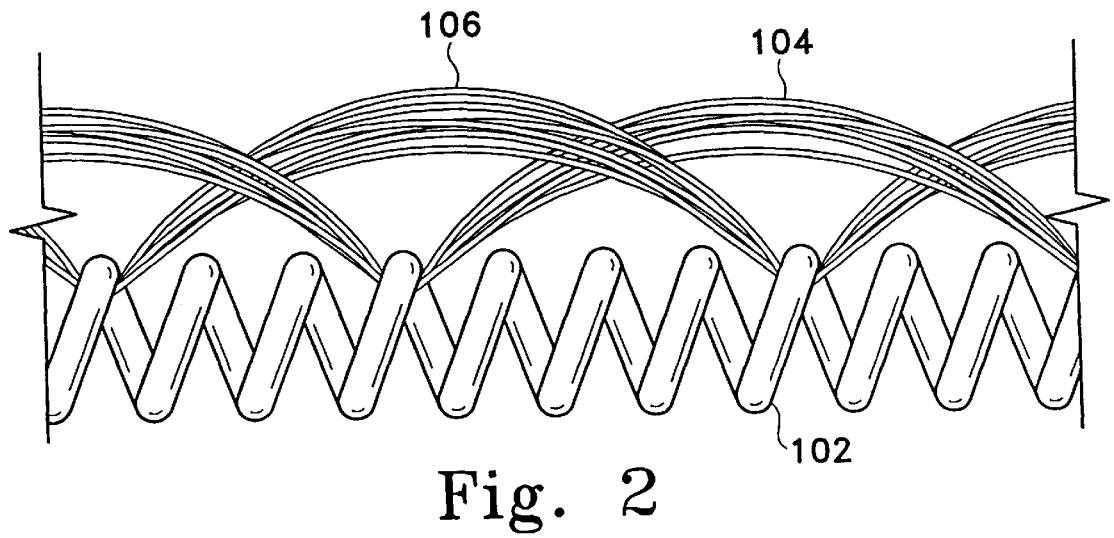
FIG. 2 shows a partial side view of the inventive coil showing details of fiber attachment.

As may be seen more clearly in FIG. 2, the multiple fiber elements are alternately looped along the coil. That is to say that the looping of the first fiber element (104) through coil (102) alternates with the looping of the second fiber element (106) through coil (102). The fiber elements may be looped through the coil (102) as shown in FIGS. 1 and 2 or they may be tied at intersections with the coil (106) although, because of the interference between the knot end catheter offered by the knot, a mere looping is preferred. The end passage of the fibers through the coil desirably involves a knot. Only a pair of fibrous elements (104 and 106) are shown in FIGS. 1 and 2; multiple such fiber elements may be used, however. Additionally, it is quite desirable that the spacing of the fibrous elements as they cross the coil need not be equal.

Figure 3:
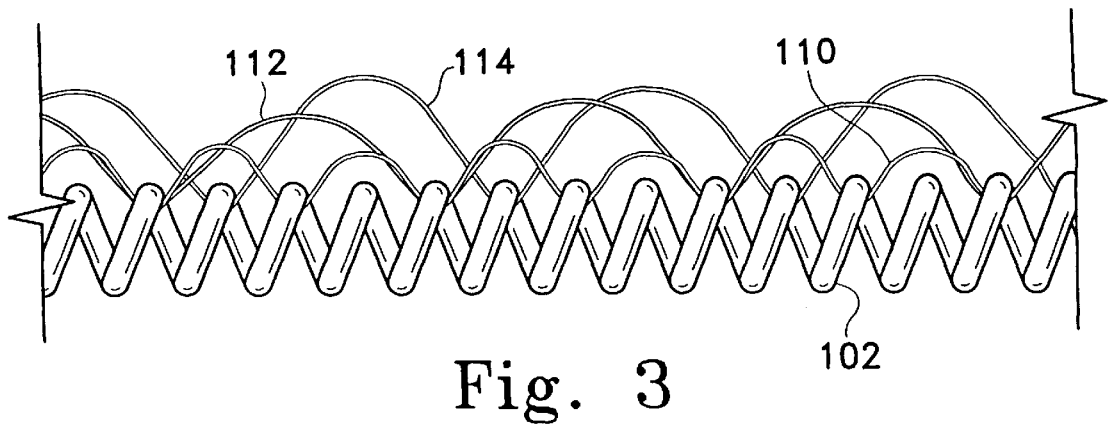
FIG. 3 shows a partial side view schematically depicting the attachment of multiple filamentary elements.

As is portrayed in the side view found in FIG. 3, multiple filament numbers having a short coil spacing (110), an intermediate coil spacing (112), and a long coil spacing (114). These various fiber spacings tend to increase the randomness of the fibered center of the randomized coil after it is released from the catheter. This benefit will be discussed in more detail below.

Figures 4, 5A, 5B, 6:
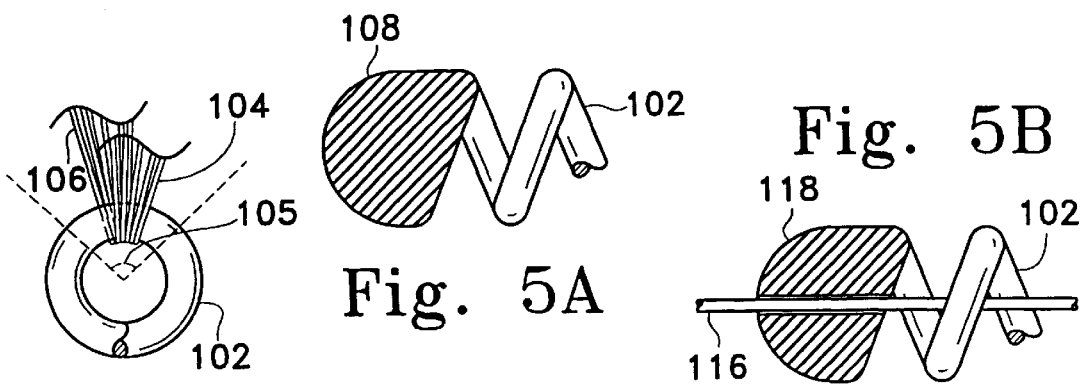
FIG. 4 shows a cross section, end view of the inventive coil showing placement of the filamentary elements.
FIGS. 5A and 5B are fragmentary cross-sections of end sections of the inventive fibered coils.
FIG. 6 shows a plan view of the relaxed inventive coil after deployment.

A significant aspect of this variation of the invention is shown in FIG. 4. That drawing, a cross-section view, shows that the various fiber elements (in this example, 104 and 106) occupy a small radial sector of the coil's circumference. Although, upon deployment, the various fiber elements will shift toward each other to a modest degree, the filaments must be placed in the same 90° quadrant (105) to attain maximum benefit of the invention. This quadrant is measured perpendicularly to the axis of the stretched coil.

Finally, FIG. 1 shows an end (108) on coil (102). Such ends (108) are typically produced by heating the end of the coil (102) to melt a small section of the coil and form a closed end (108). FIG. 5A shows a close-up of the end (108) and the coil (102).

FIG. 5B shows an additional variation in which the coil (102) encompasses a control wire (116) and an end cap (118) having a hole therethrough. Use of such a control wire (116) allows "ganging" of the coils or placement of a number of coils "nose-to-tail" within the catheter and therefore gives the attending surgeon the choice of using one or more coils without reloading the catheter.

FIG. 6 shows the shape of the coil (102) after it has been deployed from the catheter. The coil (102) encompasses an interior region (124) which has fiber passing through the region which is formed by creation of a secondary diameter (126). This region (124) of fibers provides for additional thrombogenicity in the open region (124) among the secondary coil (126) turns. This added and spaced fiber results in an enhanced thrombus formation rate—typically a matter of concern in using these devices for treatment of vascular problems. We have found that by use of this procedure of fiber attachment, upwards of 65% of the fibers found on the coil are introduced into the open region (124), preferably more than 75% and, most preferably, more than 85%.

The coils (102) discussed above are "preformed" so as to allow the coil (102) to assume the secondary diameter (126) shown in FIG. 6. The patent to Ritchart et al. (U.S. Pat. No. 4,994,069), discussed above, discusses a number of ways to preform such coils, e.g., by crimping the coil at various intervals. Another way to preform the coils, particularly when using the preferred platinum/tungsten alloy mentioned above is by winding the coil on a mandrel into the secondary diameter shown in FIG. 6 and then modestly heat-treating the thusly-wound coil. The coil will retain sufficient flexibility to extend, in a linear fashion, through a catheter lumen. Other complex coil forms having a central region may also be utilized in this invention.

Figure 7:
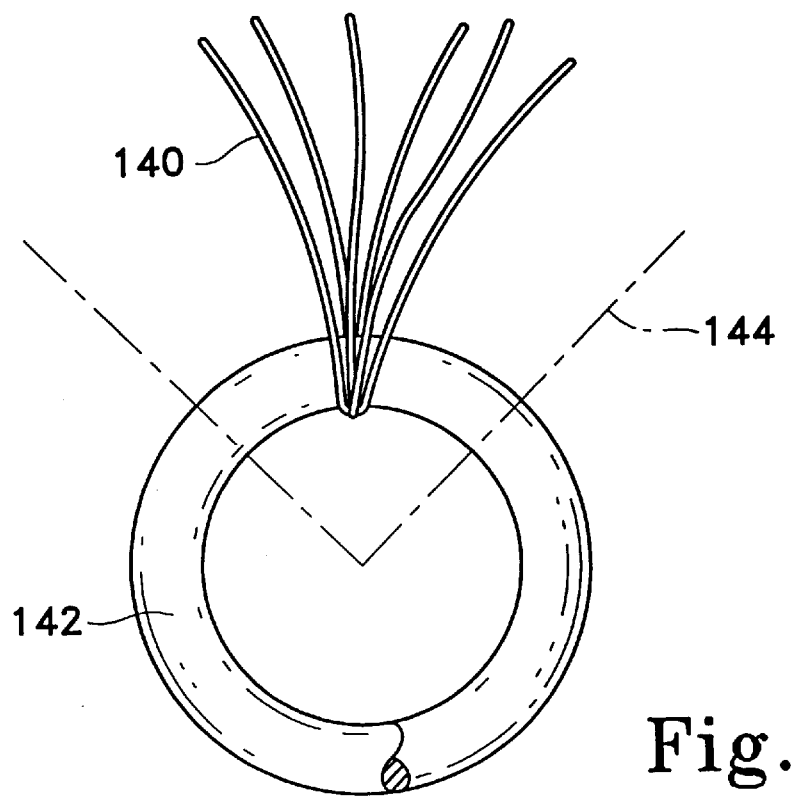
FIGS. 7, 8, and 9 show respectively end and side view of a primary form of a variation of the invention and the end view of the secondary form of that inventive coil.
Figure 8:
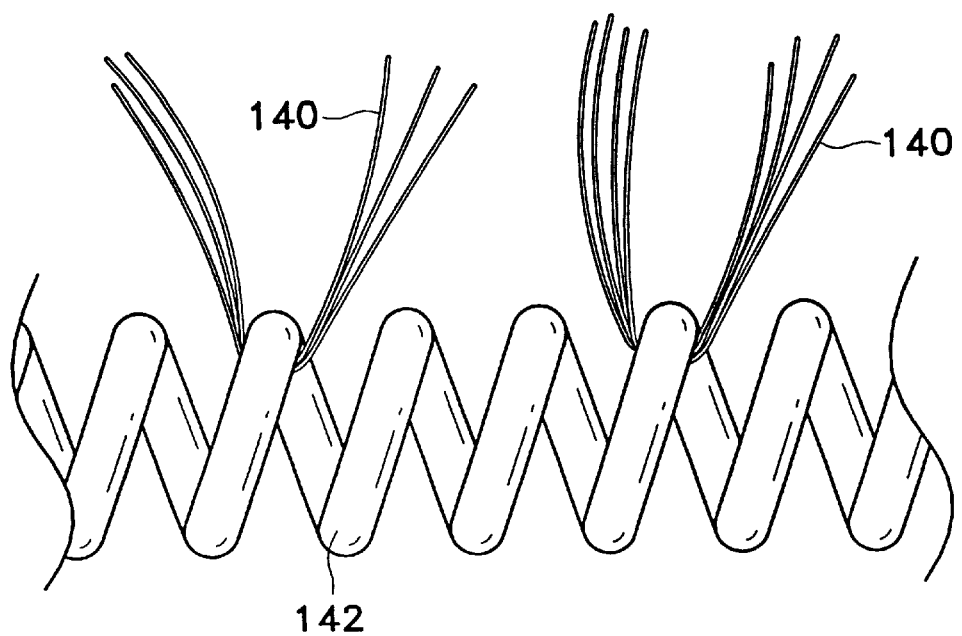
Figure 9:
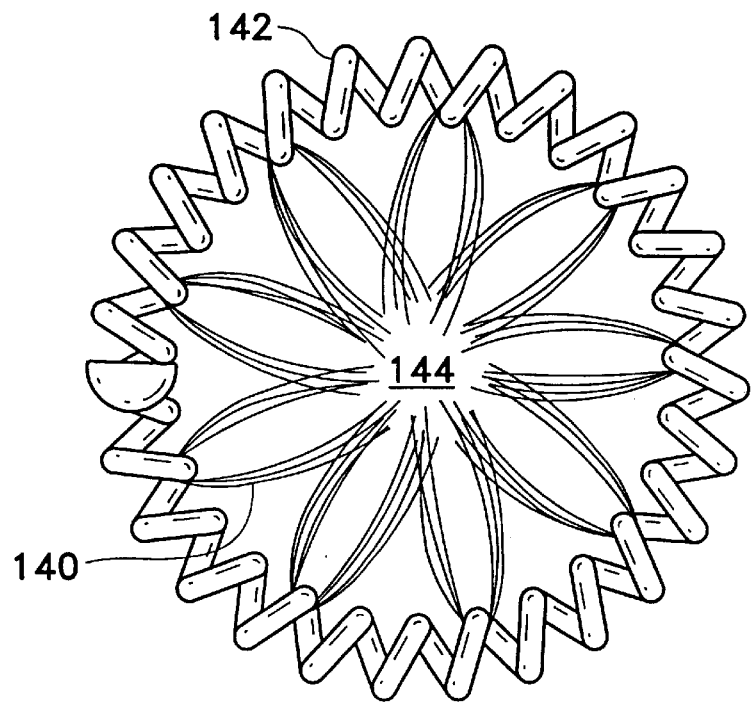

A second variation of this invention is shown in FIGS. 7–9. The materials of construction, sizes, shapes for this variation are the same or similar to those for the variation discussed above. This variation is similar to the FIG. 1–6 variation except that the fibers (140) are mounted on the coil (142) in the form of tufts. The tufts of fiber (140) are again desirably mounted in a quadrant (144) viewed along the axis of the coil. The tufts (140) are shown in FIG. 8 as being merely inserted between the turns of the coil (142). The clearance between the various turns of the coil will usually be sufficient to hold the fibers in place. However, it is also desirable to deform the polymeric material of the fibers using a heat setting procedure such as is described in U.S. patent application Ser. No. 08/431,460, to Mariant et al, the entirety of which is incorporated by reference.

The complex form of the coil (142) is shown in FIG. 9. The fibers (140) are shown within the central region (144) which is located away from the exterior of the complex coil shape.

Figure 10:
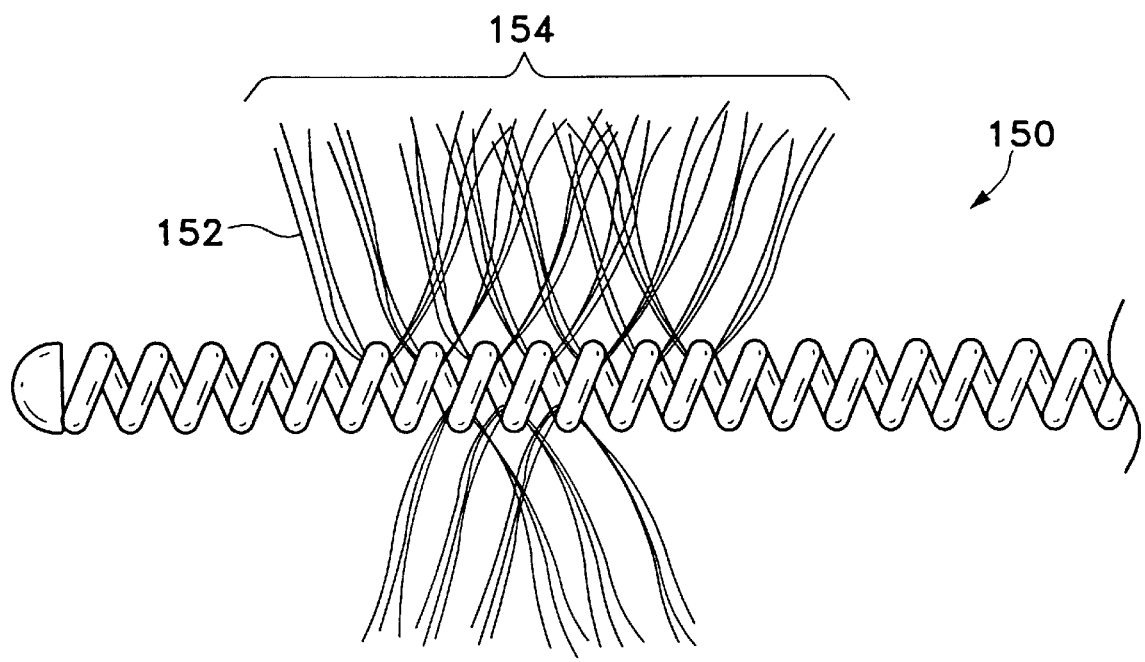
FIG. 10 shows the side view of the primary form of a tufted variation of the invention.
Figure 11:
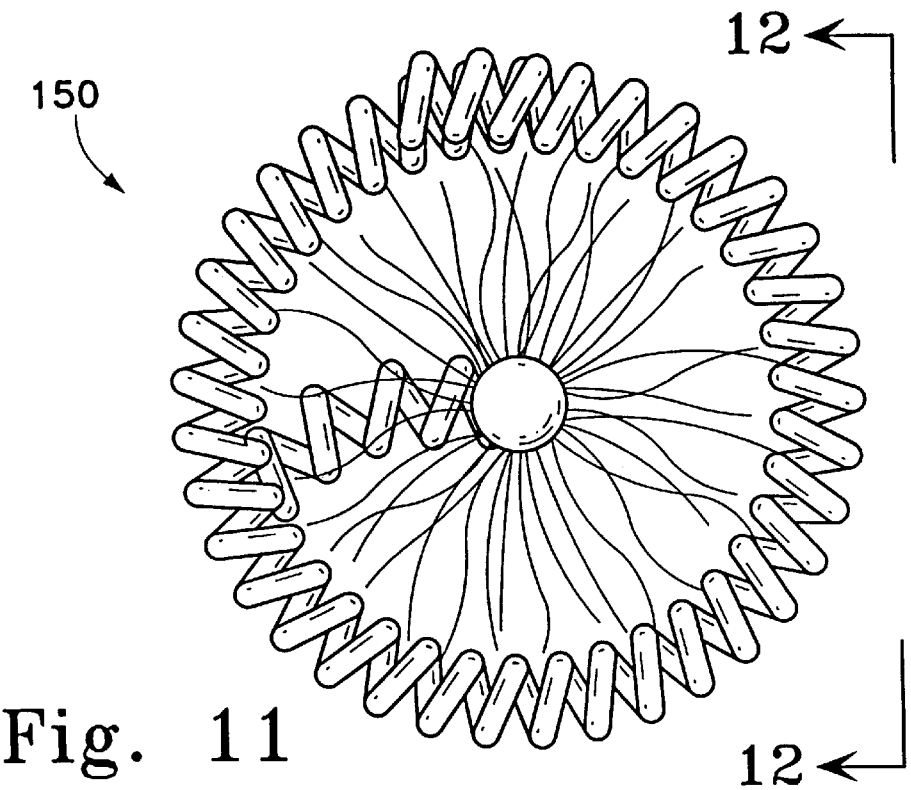
FIGS. 11 and 12 show respectively end and side views of the FIG. 10 coil.
Figure 12:
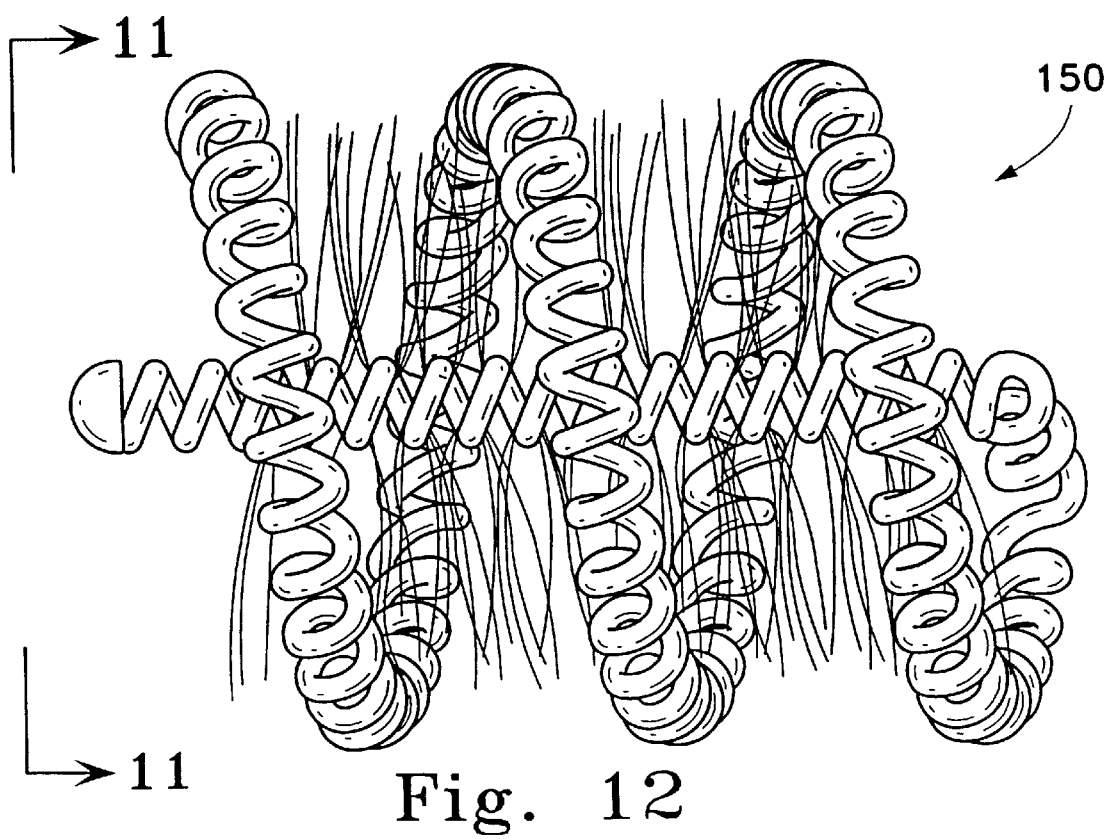

FIGS. 10–12 show a variation (150) of the invention in which the fibers (152) are placed along some portion (154) of the primary axis of the coil. The complex form of the coil assembly (150) is shown in two views in FIGS. 11 and 12. The coil is designed so that the portion (154) of the coil assembly (150) found in the interior of the relaxed complex form as shown in FIGS. 11 and 12, is interior to the coil assembly (150). The complex forms suitable for use in this invention are easily made according to any of the disclosures described above; the steps usually involving only winding the primary coil on a mandrel of suitable shape to form the secondary or complex shape and annealing at an appropriate temperature.

The variations of this device may be deployed in the same manner as are the coils described in the Ritchart et al or Chee et al patents discussed above. In general, a vascular catheter is introduced into the bloodstream at a convenient site, often the femoral artery in the groin, and advanced to the site of concern. As has been noted elsewhere, these sites ore often in the cranial arteries but may be in any other site where occlusion is desired. Guidewires are typically used to direct the catheter to the desired site but blood flow is used to direct flow-directed catheters. Once the distal end of the catheter is at the site, the catheter lumen is cleared of guidewires and the like. The inventive coil is then introduced into the lumen, often with the help of a cannula to preserve the shape of the elongated coil until it enters the catheter lumen. A pusher, typically similar in shape to a guidewire is then introduced into the catheter lumen to push the inventive coil along the interior of the catheter and out its distal end. Once the coil is safely in place, the catheter is removed from the body.

This invention has been described using specific details to augment the explanation of that invention. However, it is not our intent that the specifics so used would be in any manner limiting to the claimed invention. It is our intent that variations of the invention which would be considered equivalent to one having ordinary skill in this art be within the scope of the claims which follow.

We claim as our invention:

1. A vasoocclusive device comprising:

(a) a coil having helical windings extending between a first end and a second end, a primary coil axis extending between said first end and a second end, and defining a primary coil form, said primary coil form being self-forming into a selected secondary coil form with a secondary coil form interior, and (b) a plurality of fibrous elements attached to said coil and located with respect to said primary coil form so that upon said self-forming, the majority of said plurality of fibrous elements resides within said secondary coil form interior.

2. The vasoocclusive device of claim 1 wherein said plurality of fibrous elements are threaded through the helical coil primary form in a quadrant measured generally perpendicular to the primary coil axis.

3. The vasoocclusive device of claim 1 wherein the material making up said plurality of fibrous elements is selected from silk, cotton, polyethylene terephthalate, polylactic acid, polyglycolic acid, polyesters, fluorocarbons, and polyaramids.

4. The vasoocclusive device of claim 3 wherein the fibrous elements are polyethylene terephthalate.

5. The vasooclusive device of claim 1 wherein the secondary coil form interior contains at least about 65% of the plurality of fibrous elements.

6. The vasooclusive device of claim 1 wherein the secondary coil form interior contains at least about 85% of the plurality of fibrous elements.

7. The vasoocclusive device of claim 1 wherein said plurality of fibrous elements comprises a multiplicity of fibrillar tufts extending radially from the primary coil axis.

8. The vasoocclusive device of claim 7 wherein the multiplicity of fibrillar tufts extending radially from the primary coil axis are inserted around said helical windings.

9. The vasoocclusive device of claim 8 wherein the multiplicity of fibrillar tufts extending radially from the primary coil axis are inserted around said helical windings in a quadrant measured generally perpendicular to the coil axis.

10. The vasoocclusive device of claim 1 wherein fibers are located along only a portion of the axis of the primary coil form and that portion of the primary coil form resides within said secondary coil form interior upon said self-forming.

* * * * *